US00PP09889P

United States Patent [19]

Anderson

[11] Patent Number: Plant 9,889

[45] Date of Patent: May 13, 1997

[54] BLACK CURRANT PLANT NAMED 'BEN ALDER'

[75] Inventor: Malcolm M. Anderson, Angus, Scotland

[73] Assignee: Scottish Crop Rsearch Institute, Dundee, Scotland

[21] Appl. No.: 600,222

[22] Filed: Feb. 12, 1996

[51] Int. Cl.[6] ..... A01H 5/00

[52] U.S. Cl. ..... Plt./33.1

[58] Field of Search ..... Plt./33.1

[56] References Cited

U.S. PATENT DOCUMENTS

P.P. 5,918 3/1987 Bauer ..... Plt./33.1

*Primary Examiner*—James R. Feyrer

*Attorney, Agent, or Firm*—Burns, Doane, Swecker & Mathis, L.L.P.

[57] ABSTRACT

A new and distinct cultivar of black currant (i.e., *Ribes nigrum* L.) is provided. The flower buds of the new cultivar exhibit good tolerance to freezing during spring frosts and the time of flowering is very late. The vigorous and upright growth habit of the new cultivar renders it well amenable to mechanical harvesting. Good quality fruit is formed in high yields. The fruit exhibits an attractive glossy purple-black coloration and is particulaly well suited for juice production. Good resistance to mildew and leaf spot also are provided.

2 Drawing Sheets

SUMMARY OF THE INVENTION

The new black currant (i.e., *Ribes nigrum* L.) of the present invention was created during the course of a planned breeding program carried out during about 1972 at the Scottish Crop Research Institute, Dundee, Scotland. The female parent (i.e., the seed parent) was the product of the cross of the 'Goliath' cultivar (non-patented in the United States) by an open-pollinated specimen of the 'Ojebyn' cultivar (non-patented in the United States). The male parent (i.e., the pollen parent) was the 'Ben Lomond' cultivar (non-patented in the United States). The parentage of the new cultivar can be summarized as follows:

('Goliath'×'Ojebyn')×'Ben Lomond'.

The original plant of the new cultivar was selected during about 1976 and was found to exhibit:

(a) forms flower buds that exhibit good tolerance to freezing during spring frosts and which flower very late in the season, (b) a vigorous and upright growth habit that is amenable to mechanical fruit harvest, (c) the ability to bear glossy purple-black fruit of good quality in high yields that matures medium to late in the season and is particularly well sited for juice production, and (d) exhibits good resistance to mildew and leaf spot.

When compared to the parent 'Ben Lomond' cultivar, the new cultivar of the present invention commonly flowers at least about 6 days later, the fruit commonly ripens about 7 to 10 days later, the plant is more upright, and the plant forms slightly smaller berries of better quality with respect to color and ascorbic acid content. The ability of the flower buds of the new cultiar to well tolerate spring frosts in the absence of any significant damage is particularly noteworthy. Such characteristic was primary objective of the breeding program that resulted in the creation the new cultivar and is believed to have been inherited from its Scandinavian parent.

The new cultivar has been asexually reproduced by hardwood cuttings at the Scottish Crop Research Institute, Dundee, Scotland. Such asexual reproduction has demonstrated that the characteristics of the new cultivar are stable and are transmitted without change through succeeding propagations.

The new cultivar of the present invention initially was identified P8/12/7, and subsequently has been named the 'Ben Alder' cultivar.

BRIEF DESCRIPTION OF THE PHOTOGRAPHS

The accompanying photographs show typical specimens of the new cultivar in color as true as is reasonably possible to make the same in color illustrations of this character.

FIG. 1 shows fruit of the new cultivar in July, during about 1985. A one year-old sideshoot is shown at the left and more mature wood is shown at the center right. All fruit is purple-black in coloration and is believed to be fully ripe. The photograph was prepared at the Scottish Crop Research Institute, Dundee, Scotland.

FIG. 2 shows two branches bearing fruit of the new cultivar that were produced on one year-old wood. The fruits at the proximal end are purple-black in coloration and fully ripe and some fruits at the distal end are unripe and brownish-red in coloration. The photograph was prepared in July during about 1985 at the National Fruit Trials, Brogdale Farm, Faversham, Kent, United Kingdom.

FIG. 3 shows a typical flower/fruit bud on one year-old wood in November during about 1985 at the Scottish Crop Research Institute, Dundee, Scotland. The bark is light greyed-yellow to greyed-brown in coloration (as illustrated), and the bud scales are greyed-red in coloration (as illustrated).

FIG. 4 illustrates the shiny purple-black ripe fruit of the new cultivar while exposed for ready view in two shallow containers. The photograph was prepared in July during about 1985 at the National Fruit Trials, Brogdale Farm, Faversham. Kent, United Kingdom.

DETAILED DESCRIPTION

The following is a detailed description of the new cultivar. The specimens described were grown primarily at the Brogdale Experimental Horticulture Station, Faversham, Kent, United Kingdom. The chart used in the identification of colors is that of The Royal Horticultural Society (R.H.S. Colour Chart).

Plant:

*Growth habit.*—Upright and rounded with less spreading of the lower branches compared to the 'Ben Lomond' cultivar.

*Dimensions.*—Commonly approximately 1.4 m. in height and approximately 1.1 m. in width when fully mature. This compares to approximately 1.5 m in height and approximately 1.3 m. in width for the 'Ben Lomond' cultivar.

*Basal shoots.*—Average in number.

*Vigor.*—Strong.

Leaves:

*Leaf scars.*—Wedge-shaped and present on one year-old shoots.

*Young shoots.*—Only weak anthocyanin coloration, medium glossiness, and weak pubescence at the tip.

*Leaflets.*—Flat in transverse section, the middle rib commonly is straight, the length of the middle lobe is average, the coloration is dark green and commonly approaches Green Group 139A, medium glossiness on upper surface, the base of the blade commonly is substantially straight, and weak anthocyanin coloration commonly is present only at the base of the leaf stalk.

Flowers:

*Bud color.*—Red-Purple Group 59D.

*Bud shape.*—Ovate.

Figure 1:
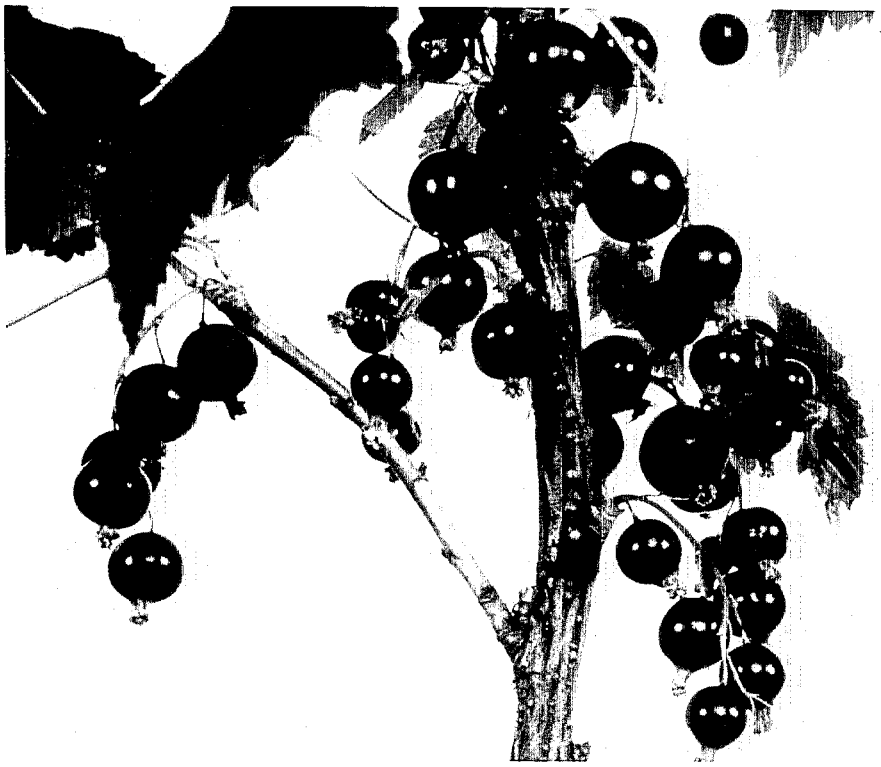
Figure 2:
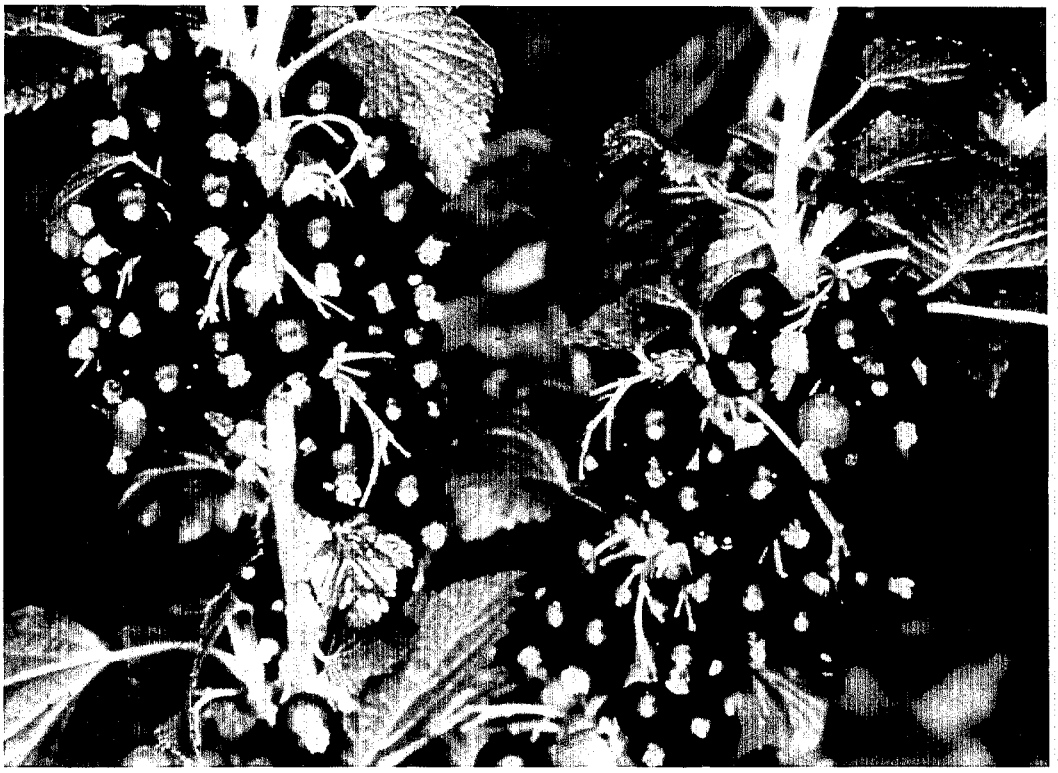
Figure 3:
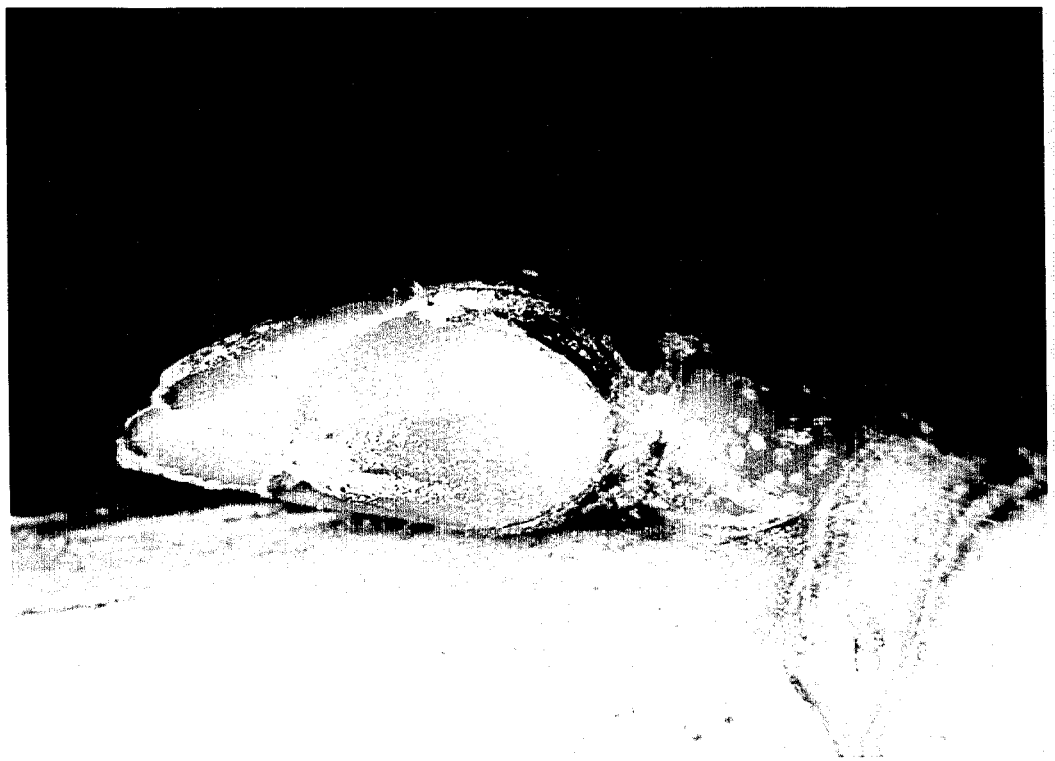
Figure 4:
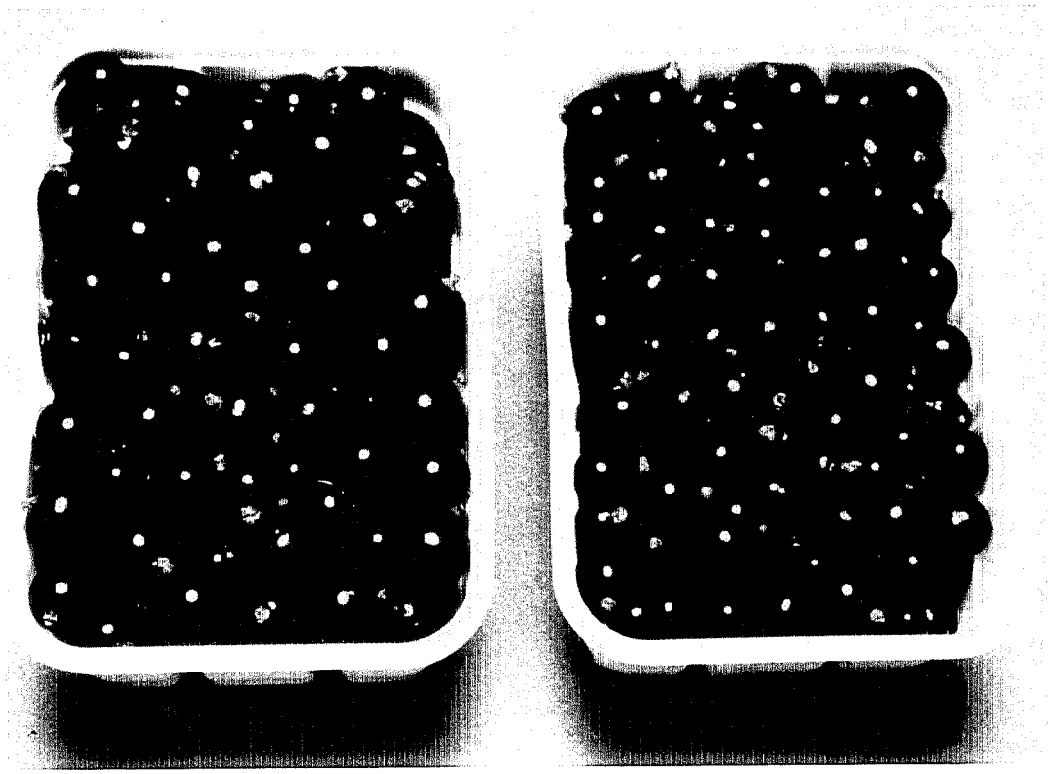

*Bud position.*—Markedly held out as illustrated in FIG. 3.

*Bud size.*—Average.

*Flowering date.*—Very late, and May 16th on average during 1987 to 1989. This compared to May 4th on average for the 'Ben Lomond' cultivar for the same years. Commonly flowers at least six days later than 'Ben Lomond'.

*Flower trusses.*—Predominantly 1 or 2 per bud.

*Sepals.*—Commonly bear an average quantity of anthocyanin coloration.

*Ovaries.*—Commonly bear a weak to average quantity of anthocyanin coloration.

Fruit:

*Size.*—Tends to be average and slightly smaller than that of the 'Ben Lomond' cultivar. For instance, commonly approximately 261 berries of the new cultivar weigh 250 grams, compared to approximately 206 berries of the 'Ben Lomond' cultivar.

*Configuration.*—Flat and rounded.

*Consistency.*—Relatively firm.

*Appearance.*—Glossy, and dark purple-black, that approaches, Black Group 202A.

*Fruit ripening.*—Medium-late. Was harvested July 29th on average during 1987 and 1988. This compares to July 22nd for the 'Ben Lomond' cultivar. Commonly ripens 7 to 10 days later than the 'Ben Lomond' cultivar.

*Anthocyanin content.*—Using Absorbance E515 the value was 1.029. This compares to 0.968 for the 'Ben Lomond' cultivar.

*Ascorbic acid content.*—125 mg./100 g. This compares to 119 mg./100 g. for the 'Ben Lomond' cultivar. Accordingly the new cultivar is superior to the 'Ben Lomond' cultivar with respect to ascorbic acid content.

*Yields.*—21.5 t/ha on average during the 1987 to 1989 National Fruit Trials, which is identical to that for the 'Ben Lomond' cultivar.

Disease resistance: Good resistance to mildew and leaf spot (i.e., *Drepanoperziza ribis*) are exhibited. Susceptibility to rust (i.e., *Cronartium ribicola*) is exhibited.

I claim:

1. A new and distinct variety of black currant plant having the following combination of characteristics:

(a) forms flower buds that exhibit good tolerance to freezing during spring frosts and which flower very late in the season, (b) a vigorous and upright growth habit is amenable to mechanical ruit harvest, (c) the ability to bear glossy purple-black fruit of good quality in high yields that matures medium to late in the season and is particularly well suited for juice production, and (d) exhibits good resistance to mildew and leaf spot;

substantially as herein shown and described.

* * * * *